United States Patent
Harrison, Jr. et al.

(10) Patent No.: US 12,178,889 B2
(45) Date of Patent: Dec. 31, 2024

(54) GOLD NANOPARTICLE-LIGAND CONJUGATES AND METHODS OF USE

(71) Applicant: The Board of Regents of the University of Oklahoma, Norman, OK (US)

(72) Inventors: Roger G. Harrison, Jr., Norman, OK (US); Needa A. Virani, Arlington, MA (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 849 days.

(21) Appl. No.: 17/269,113

(22) PCT Filed: Aug. 20, 2019

(86) PCT No.: PCT/US2019/047201
§ 371 (c)(1),
(2) Date: Feb. 17, 2021

(87) PCT Pub. No.: WO2020/041267
PCT Pub. Date: Feb. 7, 2020

(65) Prior Publication Data
US 2021/0353779 A1 Nov. 18, 2021

Related U.S. Application Data

(60) Provisional application No. 62/765,315, filed on Aug. 20, 2018.

(51) Int. Cl.
*A61K 49/04* (2006.01)
*A61K 47/69* (2017.01)

(52) U.S. Cl.
CPC ...... *A61K 49/0428* (2013.01); *A61K 47/6923* (2017.08); *A61K 47/6929* (2017.08)

(58) Field of Classification Search
CPC . A61K 47/61; A61K 47/6929; A61K 49/0428
See application file for complete search history.

(56) References Cited

U.S. PATENT DOCUMENTS

| 9,393,396 B2 | 7/2016 | Peyman |
| 2009/0098574 A1* | 4/2009 | Brisson ............... G01N 33/587 530/402 |
| 2010/0034800 A1 | 2/2010 | Kung et al. |
| 2013/0315834 A1 | 11/2013 | Praveen et al. |

OTHER PUBLICATIONS

Vijayashree et al. "Conjugation of Au Nanoparticles with Chlorambucil for Improved Anticancer Activity", Clust Sci 28, 133-148 (2017) (Year: 2016).*
Li, et al.; "Gold Nanoparticles-based SPECT/CT Imaging Probe Targeting for Vulnerable Atherosclerosis Plaques," Biomaterials (2016), 108:71-80.
International Search Report, mailed Mar. 4, 2020, in PCT/US2019/047201, filed Aug. 20, 2019.
Written Opinion of the International Searching Authority, mailed Mar. 4, 2020, in PCT/US2019/047201, filed Aug. 20, 2019.

* cited by examiner

*Primary Examiner* — James W Rogers
(74) *Attorney, Agent, or Firm* — Dunlap Codding, P.C.

(57) ABSTRACT

Gold nanoparticles are conjugated to phosphatidylserine-specific ligands for targeting and binding to surface-exposed phosphatidylserine on tumor cells and tumor vasculature. The ligand may be an annexin (e.g., annexin V). Tumor contrast is significantly increased using the targeted gold nanoparticles. Breast cancer tumors as small as 4 mm, for example, were detectable via computed tomography (CT) within 4 hours after injection of the conjugates, demonstrating usefulness of the conjugates as imaging agents. The targeted gold nanoparticle conjugate may further have a drug conjugated thereto that can be used therapeutically, for example, for cancer treatment. The gold nanoparticle conjugates can also be used for photothermal therapy and can be used in concert with an X-ray radiation treatment for cancer treatment.

3 Claims, 5 Drawing Sheets
(2 of 5 Drawing Sheet(s) Filed in Color)

GOLD NANOPARTICLE-LIGAND CONJUGATES AND METHODS OF USE

CROSS REFERENCE TO RELATED APPLICATIONS/INCORPORATION BY REFERENCE STATEMENT

This application is a US National Stage Application under 35 USC § 371 of International Application No. PCT/US2019/047201, filed Aug. 20, 2019; which claims benefit under 35 U.S.C. 119 (e) of U.S. Provisional Application Ser. No. 62/765,315, filed Aug. 20, 2018, the entirety of which is hereby expressly incorporated herein by reference.

STATEMENT REGARDING FEDERALLY SPONSORED RESEARCH OR DEVELOPMENT

Not Applicable.

BACKGROUND

Heart disease and cancer are by far the two leading causes of death in the US each year. Breast cancer is the most common form of cancer for US women and has the second highest mortality rating of cancers. It is estimated that 266,000 new cases of invasive breast cancer will be diagnosed in women in the US in 2018, and nearly 41,000 will die from invasive breast cancer in 2018. About 1 in 8 women will develop invasive breast cancer in her lifetime. Unfortunately, cancer is often detected either during late, untreatable stages or as clinically insignificant tumors due to the lack of a highly specific and sensitive detection methodology that could be commonly available to the masses for monitoring progression. These rates could be significantly reduced if tumors are caught earlier during pre-malignancy. Currently, breast cancer patients receiving aggressive treatment before tumor metastasis have a 94% survival rate. Survival rates for those with late stage, invasive tumors fall precipitously to below 10%.

The current form of breast cancer detection is annual screening of women 40-54 years old via mammograms followed by biopsies and, in some instances, magnetic resonance imaging (MRI). These multiple tests exponentially increase the costs of diagnosis for patients. In addition to the monetary costs associated with excessive testing, there are significant quality of life costs to repeated screenings. A 10-year cumulative study reported overdiagnosis rates as high as 65%. Overdiagnosis results in painful invasive screenings and treatments. Up to 77% of women reported pain during mammograms, and of these women, 11-46% declined further screening. Additionally, the high doses of radiation from repeated screenings can increase the risk of developing radiation-induced cancer. Currently, mammograms are the gold standard of diagnosis for women at risk for breast cancer; however, they fail to account for differences in breast density, which increases costs of diagnosis (follow-up biopsies and MRI), the need for repeated screenings, and the risk of overdiagnosis and overtreatment. An advantage of a computed tomography (CT) scan over mammograms is the three-dimensional imaging capability of a CT scan compared to a two-dimensional mammogram, which helps eliminate the superimposing issues with high density tissues such as tumors. Using CT is advantageous since it is available in most clinics and hospitals around the world for easy implementation and is significantly more sensitive than mammograms.

Gold nanoparticles (AuNPs) have been clinically employed as biosensors, immunological assessment tools, drug delivery agents, and for disease detection and treatment due to their high versatility. In vitro as well as in vivo studies have proven the nontoxic nature of AuNPs, which are currently in clinical trials as drug delivery and photothermal agents.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Several embodiments of the present disclosure are hereby illustrated in the appended drawings. It is to be noted, however, that the appended drawings only illustrate several typical embodiments and are therefore not intended to be considered limiting of the scope of the inventive concepts disclosed herein. The figures are not necessarily to scale, and certain features and certain views of the figures may be shown as exaggerated in scale or in schematic in the interest of clarity and conciseness.

DETAILED DESCRIPTION

Figure 1:
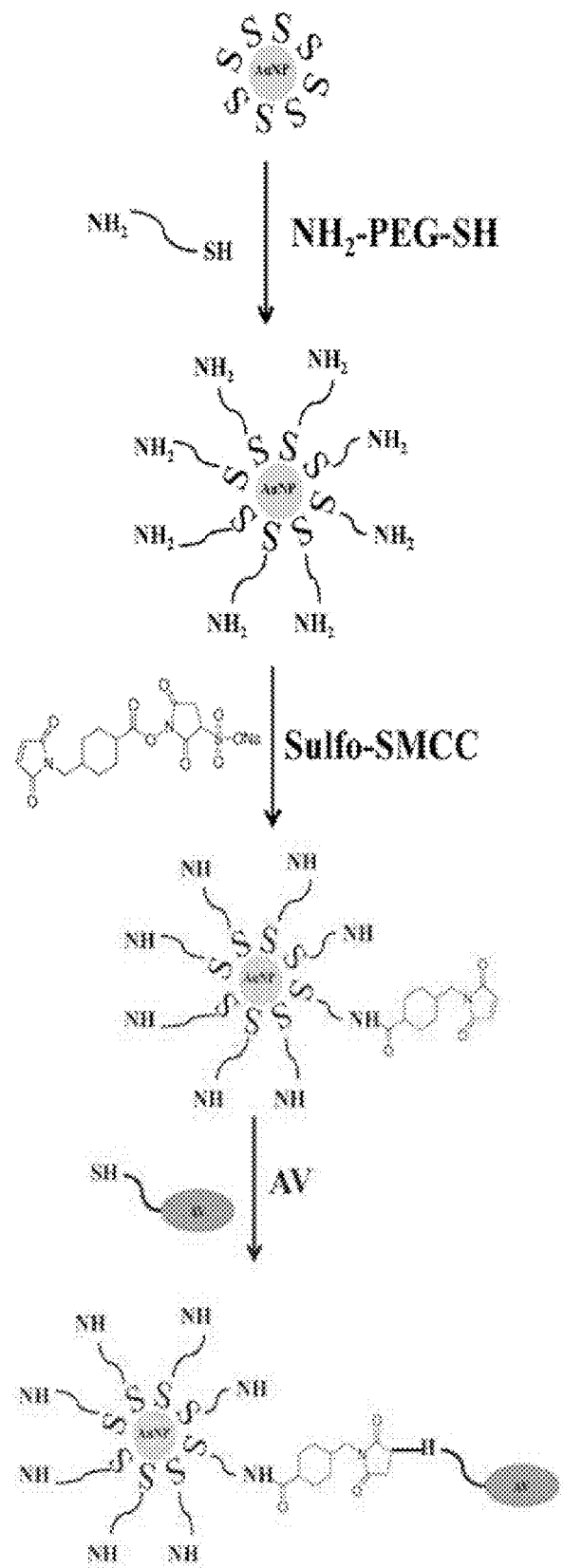
FIG. 1 is a schematic depicting synthesis of tumor-targeted gold nanoparticles (AuNP-ANXA5). ANXA5 is denoted by AV. Initially 15 nm gold nanoparticles were coated with a heterobifunctional polyethylene glycol (PEG), such as thiol PEG amine (HS-PEG-NH$_2$, also referred to herein as NH$_2$-PEG-SH), a biocompatible polymer linker. Following HS-PEG-NH$_2$ coating, sulfosuccinimidyl 4-(N-maleimidomethyl) cyclohexane-1-carboxylate (sulfo-SMCC), a heterobifunctional linker that conjugates ANXA5 to the gold nanoparticle, was bound to the amino end of the PEG, and to the ANXA5 on the other end. Any unbound PEG, sulfo-SMCC, or ANXA5 was washed off via centrifugation for a final product of AuNP-ANXA5.

The present disclosure, in at least certain non-limiting embodiments, is directed to gold nanoparticles (AuNPs) that are conjugated to phosphatidylserine-specific, cancer-targeting ligands to form targeted AuNP conjugates. The AuNP conjugates can be used, for example, as computed tomography (CT) contrast (imaging) agents for early detection of breast cancer as a more accurate and sensitive alternative to mammograms alone. The AuNP conjugates may also be used in X-ray and photothermal therapies. The AuNP conjugates may further comprise therapeutic drugs for delivering the drug to the targeted cancerous tissue.

CT scans, similar to mammograms, rely on the attenuation differences between tissues. Heavier tissues such as (but not limited to) bone attenuate more x-rays for higher contrast against surrounding soft tissues, such as (but not limited to) muscle. Since attenuation differences between normal breast tissues and tumors are very small, CT still has limitations to provide enough imaging contrast to distinguish tumors from normal breast tissue efficiently. In order to improve the contrast of tumors from the surrounding soft tissue, higher density AuNPs, which attenuate more x-rays, are specifically targeted to the malignant region as a contrast agent for CT. Thus, AuNP conjugates used in conjunction with CT provide higher sensitivity and specificity as well as minimize discrepancies in detection due to breast densities. The AuNP conjugates of the present disclosure enable detection of breast cancer tumors as small as (for example, but not by way of limitation) 4 mm in diameter. Detection of small lesions and low-grade tumors increases the survival rates of patients significantly and makes them more responsive to chemotherapy. Another advantage of the disclosed AuNP conjugates is increased sensitivity and specificity of detection, thereby minimizing the high false positive rates typical of mammograms due to the inability of a mammogram to adequately distinguish dense breast tissue from tumorous tissue. CT is widely available in all clinics and hospitals and is significantly less costly per test than a biopsy or MRI that is usually the second step in screening patients that are positive for abnormalities in mammograms or is the first form of screening for other suspected types of cancers. The AuNP conjugates of the present disclosure can also be used for detection of other cancers, such as (but not limited to) bladder, pancreas, ovarian, melanoma, brain metastases, rectal adenocarcinoma, and lung, which do not have effective diagnostic modalities that are sensitive as well as widely available. Due to a lack of a cost-effective and widely available imaging modality, most patients are diagnosed during late stages of tumor development, at which point chemotherapy is less effective.

As noted above, the AuNP conjugate may include a therapeutic drug enabling the AuNP conjugate to serve as a drug delivery vehicle. Such a tumor-targeted AuNP-drug conjugate can be used as a multimodal particle to detect and treat a tumor by targeted delivery of a chemotherapeutic to the cancer (via a cancer drug such as a cytotoxic drug conjugated to the AuNP) and to minimize significant side effects associated with currently used cancer therapies. Alternatively, the AuNP conjugate can be used as a single mode particle to image a tumor or to treat a tumor by directly delivering to the cancer a chemotherapeutic attached to the targeted AuNP. Where used herein, the term "drug" is also intended to include "prodrugs" which become activated only upon reaching the targeted site. Examples of therapeutic anti-cancer drugs which may be used in the AuNP conjugates of the present disclosure include, but are not limited to, those shown in U.S. Pat. Nos. 8,323,694 and 9,302,003.

Another use of the presently-disclosed AuNP conjugates is in photothermal treatment of tumors or thermal ablation of diseased or infected tissues. Further, because of the ability of AuNPs to absorb large amounts of X-ray radiation, the AuNP conjugates can also be used to enhance X-ray radiation therapy of cancer tumors.

Before describing various embodiments of the present disclosure by way of exemplary drawings, experimentation, results, and laboratory procedures, it is to be understood that the embodiments of the present disclosure are not limited in application to the details of compositions and methods set forth in the following description or illustrated in the drawings, experimentation, and/or results. The present disclosure is capable of other embodiments or of being practiced or carried out in various ways. As such, the language used herein is intended to be given the broadest possible scope and meaning, and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation. Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. (*Molecular Cloning: A Laboratory Manual*, 4th ed., Cold Spring Harbor Laboratory Press, Cold Spring Harbor, N.Y. (2012)) and Coligan et al. (*Current Protocols in Immunology*, Current Protocols, Wiley Interscience (1991-2017)). The nomenclatures utilized in connection with, and the laboratory procedures and techniques of, analytical chemistry, synthetic organic chemistry, molecular and cellular biology, and medicinal and pharmaceutical chemistry described herein are those well-known and commonly used in the art. Standard techniques are used for chemical syntheses, chemical analyses, pharmaceutical preparation, formulation, and delivery, and treatment of patients.

Certain abbreviations are used herein including (but not limited to): gold nanoparticles: AuNPs; annexin V or annexin A5: ANXA5; phosphatidylserine: PS; computed tomography: CT; magnetic resonance imaging: MRI; and polyethylene glycol: PEG.

All issued patents, published patent applications, and non-patent publications mentioned in the specification are indicative of the level of skill of those of ordinary skill in the art to which the presently disclosed inventive concepts pertain. All issued patents, published patent applications, and non-patent publications listed herein (including but not limited to US. Provisional Patent Application Ser. Nos. 62/765,315 filed Aug. 20, 2018, and 62/867,971, filed Jun. 28, 2019) are explicitly incorporated by reference herein to the same extent as if each individual issued patent, published patent application, or non-patent publication was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z.

Throughout this application, the terms "about" and "approximately" are used to indicate that a value includes the inherent variation of error for the composition, the method used to administer the active agent or composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The terms "about" or "approximately," where used herein when referring to a measurable value such as an amount, a temporal duration, and the like, is meant to encompass, for example, variations of ±20%, or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example. Reference to an integer with more (greater) or less than includes any number greater or less than the reference number, respectively. Thus, for example, reference to less than 100 includes 99, 98, 97, etc. all the way down to the number one (1); and less than 10 includes 9, 8, 7, etc. all the way down to the number one (1). The range 1 (unit) to 100 (units) is intended to include any sub-range therein, although that sub-range may not be explicitly designated herein. For example, since the range 1 to 100 includes all integers from 1 to 100, the sub-ranges therein include any range having a minimum value of 1 unit and any maximum value of 100 units, such as but not limited to, 5 to 75 units, 10 to 50 units, or 15 to 40 units.

As used herein, the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. A person of ordinary skill in the art will understand that typically there is no limit on the number of items or terms in any combination, unless otherwise apparent from the context.

As used herein any reference to "one embodiment" or "an embodiment" means that a particular element, feature, structure, or characteristic described in connection with the embodiment is included in at least one embodiment and may be included in other embodiments. The appearances of the phrase "in one embodiment" in various places in the specification are not necessarily all referring to the same embodiment and are not necessarily limited to a single or particular embodiment. Further, all references to one or more embodiments or examples are to be construed as non-limiting to the claims.

Where used herein the terms "specifically binds to," "specific binding," "binds specifically to," and "binding specificity," refer to the ability of a ligand (e.g., an annexin) or other agent to detectably bind to a receptor or a binding epitope while having relatively little detectable reactivity with other proteins, epitopes, or receptor structures presented on cells to which the ligand or other agent may be exposed.

As used herein, an "AuNP conjugate" refers to a particle that contains at least one receptor-binding ligand linked to a gold nanoparticle. They may be coupled directly or via a linker and/or functional group and produced by chemical coupling methods.

As used herein, the terms "conjugate(d)," "covalently coupled," "linked," "operably-linked," "bonded," "joined," and the like, with reference to the ligand and AuNP components of the AuNP conjugates of the present disclosure, mean that the specified components are either directly covalently bonded to one another or indirectly covalently bonded to one another through an intervening moiety or components, such as (but not limited to) a bridge, spacer, linker, or the like. Operably-linked moieties are associated in such a way so that the function of one moiety is not substantially affected by the other, i.e., the moieties are connected in such an arrangement that they are configured so as to perform their usual function. The two moieties may be linked directly, or may be linked indirectly via a linker sequence of molecule. For example but not by way of limitation, the ligand and the AuNP may be chemically coupled together via a thioether linkage.

Any suitable method may be used to couple or link the ligand and/or the therapeutic agent to the AuNP as long as the linked moieties retain functional activity. Non-limiting examples of linkers and linking methods are shown in U.S. Pat. Nos. 9,408,928; 9,993,553; and 10,010,618. Common molecular linkers known in the art include a maleimide or succinimide group, streptavidin, neutravidin, biotin, or similar compounds.

The term "effective amount" refers to an amount of the AuNP conjugate (which may optionally include a drug or prodrug) sufficient to exhibit a detectable imaging and/or therapeutic effect when used in the manner of the present disclosure. The effective amount for a subject will depend upon the type of subject, the subject's size and health, the nature and severity of the cancer to be treated, the method of administration, the duration of treatment, the nature of concurrent therapy (if any), the specific formulations employed, and the like. The effective amount for a given situation can be determined by one of ordinary skill in the art using routine experimentation based on the information provided herein.

The term "ameliorate" means a detectable or measurable improvement in a subject's condition or symptom thereof. A detectable or measurable improvement includes a subjective or objective decrease, reduction, inhibition, suppression, limit, or control in the occurrence, frequency, severity, progression, or duration of the condition, e.g., cancer or tumor size, or symptoms associated therewith, or an improvement in a symptom or an underlying cause or a consequence of the condition, or a reversal of the condition. A successful treatment outcome can lead to a "therapeutic effect" or "benefit" of ameliorating, decreasing, reducing, inhibiting, suppressing, limiting, controlling, or preventing the occurrence, frequency, severity, progression, or duration of a condition, or consequences of the condition in a subject.

A decrease or reduction in worsening, such as stabilizing the condition or disease, is also a successful treatment outcome. A therapeutic benefit therefore need not be complete ablation or reversal of the disease or condition, or any one, most, or all adverse symptoms, complications, consequences, or underlying causes associated with the disease or condition. Thus, a satisfactory endpoint may be achieved when there is an incremental improvement such as a partial decrease, reduction, inhibition, suppression, limit, control, or prevention in the occurrence, frequency, severity, progression, or duration, or inhibition or reversal of the condition or disease (e.g., stabilizing), over a short or long duration of time (hours, days, weeks, months, etc.). Effectiveness of a method or use, such as a treatment that provides a potential therapeutic benefit or improvement of a condition or disease, can be ascertained by various methods and testing assays.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular non-limiting examples of such cancers include squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma, and various types of head and neck cancer.

The AuNP conjugate treatments disclosed herein may be used concurrently with other anti-cancer therapies. As used herein, the term "concurrent therapy" is used interchangeably with the terms "combination therapy" and "adjunct therapy," and will be understood to mean that the patient in need of treatment is treated or given another drug for the disease in conjunction with the AuNP conjugates of the present disclosure, such as (but not limited to) chemotherapy and/or immunotherapy, and with or without immunostimulants. This concurrent therapy can be sequential therapy, where the patient is treated first with one drug and then another drug, or the two or more drugs can be given simultaneously.

The terms "administration" and "administering" as used herein will be understood to include all routes of administration known in the art, including but not limited to, oral, topical, transdermal, parenteral, subcutaneous, intranasal, mucosal, intramuscular, intraperitoneal, intravitreal, and intravenous routes, including both local and systemic applications. In addition, the compositions of the present disclosure (and/or the methods of administration of same) may be designed to provide delayed, controlled, or sustained release using formulation techniques which are well known in the art.

The term "pharmaceutically acceptable" refers to compounds and compositions which are suitable for administration to humans and/or animals without undue adverse side effects.

By "biologically active" is meant the ability to modify the physiological system of an organism. A molecule can be biologically active through its own functionalities, or may be biologically active based on its ability to activate or inhibit molecules having their own biological activity.

As used herein, "substantially pure" means an object species is the predominant species present (i.e., on a molar basis, it is more abundant than any other individual species in the composition). In certain non-limiting embodiments, a substantially purified fraction is a composition wherein the object species comprises at least about 50 percent (on a molar basis) of all macromolecular species present. In certain non-limiting embodiments, a substantially pure composition will comprise more than about 80 percent of all macromolecular species present in the composition, or more than about 85%, or more than about 90%, or more than about 95%, or more than about 99% of all macromolecular species present in the composition.

A "liposome" is a small vesicle composed of various types of lipids, phospholipids, and/or surfactant. The components of the liposome are commonly arranged in a bilayer formation, similar to the lipid arrangement of biological membranes.

The term "subject" is used interchangeably herein with the term "patient" and includes human and veterinary subjects including any animal subject to a cancerous tumor. For purposes of treatment, the term "mammal" as used herein refers to any animal classified as a mammal, including (but not limited to) humans, non-human primates, monkeys, domestic animals (such as, but not limited to, dogs and cats), experimental mammals (such as, but not limited to, mice, rats, rabbits, guinea pigs, and chinchillas), farm animals (such as, but not limited to, horses, pigs, cattle, goats, sheep, and llamas), and any other animal that has mammary tissue.

Certain non-limiting embodiments of the present disclosure are directed to a gold nanoparticle (AuNP) conjugate that includes an AuNP having a functional group and/or linker group on a surface thereof. The AuNP conjugate also includes a phosphatidylserine-specific ligand conjugated to the AuNP via the functional group and/or linker group on the surface of the AuNP. In one particular (but non-limiting) embodiment, the phosphatidylserine-specific ligand is an annexin, such as (but not limited to) annexin V.

The terms "gold nanoparticle" and "AuNP" are used interchangeably herein and generally refer to a particle having a size in a range of from about 1 nm to about 300 nm, about 400 nm, about 500 nm, about 600 nm, about 700 nm, about 800 nm, about 900 nm, or about 1000 nm. In certain non-limiting embodiments, the AuNPs of the AuNP conjugate may have a size in a range of from about 5 nm to about 100 nm, or a range of from about 5 nm to about 60 nm, or a range of from about 10 nm to about 30 nm. In addition, the AuNPs of the AuNP conjugate composition may have an average size in a range of from about 5 nm to about 100 nm, or a range of from about 5 nm to about 60 nm, or a range of from about 10 nm to about 30 nm. Further non-limiting examples and dimensions of AuNPs that may be used in the compositions of the present disclosure are shown in U.S. Pat. No. 8,323,694. The term "gold nanoparticle" as referred to herein includes particles having a gold metal organic framework having at least one dimension measuring less than one micron in length. Nanoparticles include conventionally known nanoparticles such as nanorods, nanospheres, and nanoplatelets, or the nanoparticles may have any other three-dimensional shape.

Functional groups are groups that can be covalently linked and/or bonded to the AuNPs for covalently or electrostatically-linking to the therapeutic and/or targeting ligand. The functional groups include any group that can be reacted with another compound to form a covalent linkage between the compound and the AuNP. Examples of such functional groups include, but are not limited to, carboxylic acids and carboxylic acid salt derivatives, acid halides, sulfonic acids and sulfonic acid salts, anhydride derivatives, hydroxyl derivatives, amine and amide derivatives, silane derivations, phosphate derivatives, nitro derivatives, succinimide and sulfo-containing succinimide derivatives, halide derivatives, alkene derivatives, morpholine derivatives, cyano derivatives, epoxide derivatives, ester derivatives, carbazole derivatives, azide derivatives, alkyne derivatives, acid containing sugar derivatives, glycerol analogue derivatives, maleimide derivatives, protected acids and alcohols, acid halide derivatives, and combinations thereof. The functional groups can be substituted or unsubstituted.

Alternatively, functional groups can be attached to AuNP via a linker. The term "linker" as used herein refers to any chemical structure that can be placed between a surface of the AuNP and the functional group. For example, linkers may be selected from the group including polyethylene glycol (PEG), alkyl, substituted alkyl, alkoxy, substituted alkoxy, acyl, substituted acyl, acylamino, substituted acylamino, alkylamino, substituted alkylamino, alkylsulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy, substituted heteroaryloxyalkyl groups, and combinations thereof. In various non-limited exemplary embodiments, the groups can be from C1 to C30, such as (but not limited to) C1 to C10, or C1 to C20.

Where used herein, the term "annexin" refers to any of annexins 1-11 and 13, which are more particularly designated as annexins A1, A2, A3, A4, A5, A6, A7, A8, A9, A10, A11, and A13. Annexin I and annexin V, where used herein, refer to Annexin A1 and Annexin A5, respectively, for example. The annexins contemplated for use herein include both human annexins and non-human cognate orthologs of annexins A1-A11 and A13 from non-human vertebrates, including but not limited to, non-human primates, dogs, cats, horses, livestock animals, and zoo animals, which may be used for treatment in said non-human mammals in the methods contemplated herein. The annexins contemplated for use herein are discussed in further detail in V. Gerke and S. E. Moss (*Physiol. Rev.*, (2002) 82:331-371). The AuNP conjugates of the present disclosure may also include fragments of annexins, instead of an entire annexin, as long as the fragment retains the PS binding activity of an entire annexin.

Annexin V (and other annexins) binds with very high affinity to PS-containing phospholipid bilayers. Annexin V may be obtained, for example, as described in U.S. Pat. No. 7,393,833, issued to Lind et al. on Jul. 1, 2008.

Examples of other PS-binding proteins that can be used in substitution include (but are not limited to) those in the Annexin family (listed above), lactadherin, domains found in proteins known to bind PS, such as Factor V/Va, Factor X/Xa, Factor II/IIa, Factor VII/VIIa, Factor IX/IXa, Factor VIII/VIIIa, Spectrin, Class B Scavenger receptor type I, Protein Kinase C, and proteins containing the C2 domains of protein kinase C (this includes synaptotagmins), Rabphilin family members, the PS receptor, endothelial lectin-like OxLDL receptor-1 (LOX-1), antibodies to PS, phosphatidylserine decarboxylase, MARCKS (myristoylated, alanine-rich protein kinase C substrate), PS-p68, Myosin, Erythrocyte protein 4.1, hemoglobin, Calponin family members, S100A, S100B, calcyclin-binding protein family members, milk membrane-glycoprotein, MFG-E8 (milk fat globule-EGF factor 8), and other PS-binding motifs known to those of ordinary skill in the art.

Alternatively, the PS-specific ligand of the AuNP conjugate of the present disclosure may be an anionic phospholipid-specific antibody, such as a PS-specific monoclonal antibody. Examples of PS-specific monoclonal antibodies include those described in U.S. Pat. Nos. 6,312,694; 6,406, 693; 6,783,760; 6,818,213; and 7,067,109. The ligand may be a non-PS-binding moiety which binds to another tumor specific feature, such as those described in U.S. Pat. Nos. 6,451,312; 6,093,399; 6,004,555; and 6,051,230. The ligands of the present disclosure may be targeted to other tumor/cancer specific external receptors other than anionic phospholipids. Such receptors include, for example, those described in U.S. Pat. Nos. 6,818,213; 6,783,760; 6,451,312; and 6,406,693. As noted above, all of the patents, published applications, and publications listed herein are hereby expressly incorporated herein by reference in their entireties.

The modification of one of the receptor-binding ligands described herein above to provide a fragment or variant thereof that substantially maintains the receptor binding ability of the native receptor-binding ligand is fully within the skill of a person in the art and therefore is also within the scope of the present disclosure. The term "substantially maintains the receptor-binding ability of the native receptor-binding ligand" means that the protein fragment or variant maintains at least 50% of the native ligand's receptor-binding ability, at least 75% of the native ligand's receptor-binding ability, at least 90% of the native ligand's receptor-binding ability, or at least 95% of the native ligand's receptor-binding ability.

Certain non-limiting embodiments of the present disclosure are directed to an imaging agent that includes a phosphatidylserine-specific ligand conjugated to a gold nanoparticle. Any phosphatidylserine-specific ligand described or otherwise contemplated herein may be utilized in accordance with the present disclosure. In one particular (but non-limiting) embodiment, the phosphatidylserine-specific ligand is an annexin (such as, but not limited to, annexin V). In one particular (but non-limiting) embodiment, the imaging agent comprises any of the AuNP conjugates described or otherwise contemplated herein.

Certain non-limiting embodiments of the present disclosure are directed to a therapeutic composition that comprises any of the AuNP conjugates described or otherwise contemplated herein, and that further comprises a therapeutic drug conjugated to at least one of the phosphatidylserine-specific ligand and the AuNP. In a particular (but non-limiting) embodiment, the phosphatidylserine-specific ligand is an annexin (such as, but not limited to, annexin V).

Certain non-limiting embodiments of the present disclosure are directed to a composition (such as, but not limited to, a pharmaceutical composition) that comprises any of the AuNP conjugates, imaging agents, or therapeutic compositions described or otherwise contemplated herein and that further comprises a pharmaceutically-acceptable carrier, diluent, vehicle, or excipient in which the AuNP conjugate/imaging agent/therapeutic composition is disposed. In a particular (but non-limiting) embodiment, the phosphatidylserine-specific ligand is an annexin (such as, but not limited to, annexin V).

Certain non-limiting embodiments of the present disclosure are directed to a method of computed tomography (CT) imaging of a subject. The method includes the steps of administering to the subject any of the AuNP conjugates/imaging agents (or compositions containing same) described or otherwise contemplated herein; allowing the AuNP conjugates/imaging agents (or compositions containing same) to bind to and/or penetrate into a tissue of the subject, wherein the tissue is suspected of containing a cancer; and collecting a CT image of the tissue suspected of containing the cancer. In particular (but non-limiting) embodiments, the tissue is selected from the group consisting of tissues of the myocardium, brain, breast, prostate, ovary, uterus, colon, pancreas, liver, intestine, kidney, spleen, limb, lung, and combinations thereof. In particular (but non-limiting) embodiments, the AuNP conjugate binds to phosphatidylserine that is externally exposed on a tumor vasculature cell.

Certain non-limiting embodiments of the present disclosure are directed to a method of therapeutic treatment of imaging of a cancerous tumor in a subject in need of such therapy. In the method, any of the AuNP conjugates/imaging agents (or compositions containing same) described or otherwise contemplated herein is administered to the subject. In a particular (but non-limiting) embodiment, one of the therapeutic compositions described or otherwise contemplated herein (and which includes a therapeutic compound conjugated to the AuNP conjugate) is administered to the subject.

Certain non-limiting embodiments of the present disclosure are directed to an X-ray radiation treatment method. The method comprises the steps of: administering to a subject in need of X-ray radiation therapy any of the AuNP conjugates/imaging agents (or compositions containing same) described or otherwise contemplated herein; allowing the AuNP conjugates/imaging agents to bind to and/or penetrate into a cancerous tissue of the subject; and exposing a dosage of X-ray radiation to the cancerous tissue.

Certain non-limiting embodiments of the present disclosure are directed to a method of photothermal therapy for treating a cancerous tissue in a subject in need of such therapy. The method comprises the steps of: administering to the subject any of the AuNP conjugates/imaging agents (or compositions containing same) disclosed or otherwise contemplated herein; allowing the AuNP conjugates/imaging agents to bind to and/or penetrate into the cancerous tissue of the subject; and exposing the subject to a dosage of electromagnetic radiation comprising a wavelength absorbable by the gold nanoparticle of the AuNP conjugate/imaging agent, thereby causing elevation of the temperature of the gold nanoparticle to a temperature which induces damage to and/or death of the cancerous tissue to which the AuNP conjugate is bound and/or into which the AuNP conjugate has penetrated.

Any wavelength of electromagnetic radiation that allows the AuNP conjugate to function in accordance with the present disclosure of provide photothermal therapy for treatment of a cancerous tissue can be utilized in accordance with the present disclosure. In particular (but non-limiting) embodiments, the wavelength of electromagnetic radiation is in a range of from about 300 nm to about 1100 nm, or in a range of from about 700 nm to about 800 nm.

Practice of the methods of the present disclosure may comprise administering to a subject an effective amount of a drug-containing AuNP conjugate in any suitable systemic and/or local formulation, in an amount effective to deliver the dosages listed herein, or other acceptable dosages as determined by the attending physician. An effective amount of an active agent (i.e., drug) of the present disclosure will generally contain sufficient active agent to deliver, in certain non-limiting embodiments, from about 0.1 µg/kg to about 1000 mg/kg (mass of active agent/body weight of the subject). Particularly (but not by way of limitation), the composition will deliver about 0.5 µg/kg to about 100 mg/kg, and more particularly about 1 µg/kg to about 10 mg/kg. The dosage can be administered, for example but not by way of limitation, on a one-time basis, or administered at multiple times (for example but not by way of limitation, from one to five times per day, or once or twice per week), or continuously via a venous drip, depending on the desired therapeutic effect. In one non-limiting embodiment of a therapeutic method, the active agent is provided in an IV infusion in the range of from about 0.1 µg/kg to about 10 mg/kg to about 100 mg/kg to about 1000 mg/kg of body weight once a day.

Administration of the active agent used in the pharmaceutical composition or to practice the method of the present disclosure can be carried out in a variety of conventional ways, such as, but not limited to, orally, by inhalation, rectally, or by cutaneous, subcutaneous, intraperitoneal, or intravenous injection. Oral formulations may be formulated such that the active agent passes through a portion of the digestive system before being released, for example, it may not be released until reaching the small intestine or the colon.

When an effective amount of the active agent is administered orally, it may be in the form of a solid or liquid preparation such as (but not limited to) capsules, pills, tablets, lozenges, melts, powders, suspensions, solutions, elixirs, or emulsions. Solid unit dosage forms can be capsules of the ordinary gelatin type containing, for example, surfactants, lubricants, and inert fillers such as lactose, sucrose, and cornstarch, or the dosage forms can be sustained release preparations. The pharmaceutical composition may contain a solid carrier, such as (but not limited to) a gelatin or an adjuvant. The tablet, capsule, and powder may contain from about 0.05% to about 95% of the active substance compound by dry weight. When administered in liquid form, a liquid carrier such as (but not limited to) water, petroleum, oils of animal or plant origin (such as, but not limited to, peanut oil, mineral oil, soybean oil, or sesame oil), or synthetic oils may be added. The liquid form of the pharmaceutical composition may further contain physiological saline solution, dextrose, or other saccharide solution, or one or more glycols (such as, but not limited to, ethylene glycol, propylene glycol, or polyethylene glycol). When administered in liquid form, the pharmaceutical composition particularly contains from about 0.005% to about 95% by weight of the active agent. For example, a dose of about 10 mg to about 1000 mg once or twice a day could be administered orally.

In another non-limiting embodiment, the AuNP conjugates described herein can be tableted with conventional tablet bases such as (but not limited to) lactose, sucrose, and cornstarch in combination with binders (such as, but not limited to, acacia, cornstarch, or gelatin), disintegrating agents (such as, but not limited to, potato starch or alginic acid), and a lubricant (such as, but not limited to, stearic acid or magnesium stearate). Liquid preparations are prepared by dissolving the active agent in an aqueous or non-aqueous pharmaceutically acceptable solvent which may also contain (for example, but not by way of limitation) suspending agents, sweetening agents, flavoring agents, and preservative agents as are known in the art.

For parenteral administration, for example, the AuNP conjugates of the present disclosure may be disposed in a physiologically acceptable pharmaceutical carrier and administered as either a solution or a suspension. Illustrative of suitable pharmaceutical carriers include (but are not limited to) water, saline, dextrose solutions, fructose solutions, ethanol, or oils of animal, vegetative, or synthetic origin. The pharmaceutical carrier may also contain (for example, but not by way of limitation) preservatives and buffers as are known in the art.

When an effective amount of the AuNP conjugate is administered by intravenous, cutaneous, or subcutaneous injection, the active agent may be in the form of a pyrogen-free, parenterally acceptable aqueous solution or suspension. The preparation of such parenterally acceptable solutions, having due regard to pH, isotonicity, stability, and the like, is well within the skill in the art. A particular pharmaceutical composition for intravenous, cutaneous, or subcutaneous injection may contain, in addition to the active agent, an isotonic vehicle such as (but not limited to) Sodium Chloride Injection, Ringer's Injection, Dextrose Injection, Dextrose and Sodium Chloride Injection, Lactated Ringer's Injection, or other vehicle as known in the art. The pharmaceutical composition of the present disclosure may also contain stabilizers, preservatives, buffers, antioxidants, or other additives known to those of skill in the art.

As noted, particular amounts and modes of administration can be determined by one of ordinary skill in the art. A person of ordinary skill in the art of preparing formulations can readily select the proper form and mode of administration, depending upon the particular characteristics of the active agent selected, the condition to be treated, the stage of the condition, and other relevant circumstances using formulation technology known in the art, described, for example, in Remington: The Science and Practice of Pharmacy, 22nd ed.

Additional pharmaceutical methods may be employed to control the duration of action of the active agent. Increased half-life and/or controlled release preparations may be achieved through the use of polymers to conjugate, complex with, and/or absorb the active agent described herein. The controlled delivery and/or increased half-life may be achieved by selecting appropriate macromolecules (for example but not by way of limitation, polysaccharides, polyesters, polyamino acids, homopolymers polyvinyl pyrrolidone, ethylenevinylacetate, methylcellulose, or carboxymethylcellulose, and acrylamides such as N-(2-hydroxypropyl) methacrylamide), and the appropriate concentration of macromolecules as well as the methods of incorporation, in order to control release. The active agent may also be ionically or covalently conjugated to the macromolecules described above.

Possible methods useful in controlling the duration of action of the active agent by controlled release preparations and half-life include incorporation of the active agent into particles of a polymeric material. Non-limiting examples of polymeric materials that may be used in accordance with the present disclosure include polyesters, polyamides, polyamino acids, hydrogels, poly(lactic acid), ethylene vinylacetate copolymers, and copolymer micelles of, for example, polyethylene glycol (PEG) and poly(l-aspartamide).

It is also possible to entrap the active agent in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles, and nanocapsules), or in macroemulsions. Such techniques are well known to persons having ordinary skill in the art.

When the AuNP conjugate is to be used as an injectable material, it can be formulated into a conventional injectable carrier. Suitable carriers include (but are not limited to) biocompatible and pharmaceutically acceptable phosphate buffered saline solutions, which are particularly isotonic.

The AuNP conjugate may be formulated in a composition that includes a sterile diluent, which may contain materials generally recognized for approximating physiological conditions and/or as required by governmental regulation. In this respect, the sterile diluent may contain a buffering agent to obtain a physiologically acceptable pH, such as (but not limited to) sodium chloride, saline, phosphate-buffered saline, and/or other substances which are physiologically acceptable and/or safe for use. In general, the material for intravenous injection in humans should conform to regulations established by the Food and Drug Administration, which are available to those in the field. The pharmaceutical composition may also be in the form of an aqueous solution containing many of the same substances as described above.

The AuNP conjugate of the present disclosure can also be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines, and substituted ethanolamines.

Examples of cytotoxic drugs that can be used in the AuNP conjugates of the present disclosure include, but are not limited to, in general, alkylating agents, anti-proliferative agents, tubulin binding agents and the like, for example, the anthracycline family of drugs, the vinca drugs, the mitomycins, the bleomycins, the cytotoxic nucleosides, the pteridine family of drugs, diynenes, and the podophyllotoxins. Examples of those groups include, adriamycin, carminomycin, daunorubicin, aminopterin, methotrexate, methopterin, dichloromethotrexate, mitomycin C, porfiromycin, 5-fluorouracil, 6-mercaptopurine, cytosine arabinoside, podophyllotoxin, or podophyllotoxin derivatives such as etoposide or etoposide phosphate, melphalan, vinblastine, vincristine, leurosidine, vindesine, leurosine, and the like. The drug may be selected from camptothecin, homocamptothecin, colchicine, combretastatin, dolistatin, doxorubicin, methotrexate, podophyllotixin, rhizoxin, rhizoxin D, a taxol, paclitaxol, CC1065, or a maytansinoid, and derivatives and analogs thereof.

The drug used in the AuNP conjugates of the present disclosure may be an antineoplastic agent such as Acivicin; Aclarubicin; Acodazole Hydrochloride; Acronine; Adozelesin; Adriamycin; Aldesleukin; Altretamine; Ambomycin; A. metantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Camptothecin; Caracemide; Carbetimer; Carboplatin; Carmustine; Carubicin Hydrochloride; Carzelesin; Cedefingol; Chlorambucil; Cirolemycin; Cisplatin; Cladribine; Colchicine; Combretestatin A-4; Crisnatol Mesylate; Cyclophosphamide; Cytarabine; Dacarbazine; DACA (N-[2-(Dimethyl-amino)ethyl] acridine-4-carboxamide); Dactinomycin; Daunorubicin Hydrochloride; Daunomycin; Decitabine; Dexormaplatin; Dezaguanine; Dezaguanine Mesylate; Diaziquone; Docetaxel; Dolasatins; Doxorubicin; Doxorubicin Hydrochloride; Droloxifene; Droloxifene Citrate; Dromostanolone Propionate; Duazomycin; Edatrexate; Eflornithine Hydrochloride; Ellipticine; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Flurocitabine; Fosquidone; Fostriecin Sodium; Gemcitabine; Gemcitabine Hydrochloride; Gold Au 198; Homocamptothecin; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; PeploycinSulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Rhizoxin; Rhizoxin D; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiocolchicine; Thiamiprine; Thioguanine; Thiotepa; Thymitaq; Tiazofurin; Tirapazamine; Tomudex; TOP53; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine; Vinblastine Sulfate; Vincristine; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2' Deoxyformycin; 9-aminocamptothecin; raltitrexed; N-propargyl-5,8-dideazafolic acid; 2-chloro-2'-arabino-fluoro-2'-deoxyadenosine; 2-chloro-2'-deoxyadenosine; anisomycin; trichostatin A; hPRL-G129R; CEP-751; linomide; sulfur mustard; nitrogen mustard (mechlorethamine); cyclophosphamide; melphalan; chlorambucil; ifosfamide; busulfan; N-methyl-N-nitrosourea (MNU); N, N'-Bis (2-chloroethyl)-N-nitrosourea (BCNU); N-(2-chloroethyl)-N' cyclohexyl-N-nitrosourea (CCNU); N-(2-chloroethyl)-N'-(trans-4-methyl-cyclohexyl-N-nitrosourea (MeCCNU); N-(2-chloroethyl)-N'-(diethyl) ethylphosphonate-N-nitrosourea (fotemustine); streptozotocin; diacarbazine (DTIC); mitozolomide; temozolomide; thiotepa; mitomycin C; AZQ; adozelesin; Cisplatin; Carboplatin; Ormaplatin; Oxaliplatin; C1-973; DWA 2114R; JM216; JM335; Bis (platinum); tomudex; azacitidine; cytarabine; gemcitabine; 6-Mercaptopurine; 6-Thioguanine; Hypoxanthine; teniposide 9-amino camptothecin; Topotecan; CPT-11; Doxorubicin; Daunomycin; Epirubicin; darubicin; mitoxantrone; losoxantrone; Dactinomycin (Actinomycin D); amsacrine; pyrazoloacridine; all-trans apthal; 14-hydroxy-retro-retinol; all-trans retinoic acid; N-(4-Hydroxyphenyl) retinamide; 13-cis retinoic acid; 3-Methyl TTNEB; 9-cis retinoic acid; fludarabine (2-F-ara-AMP); or 2-chlorodeoxyadenosine (2-Cda).

Other suitable anti-neoplastic compounds that can be used in the AuNP conjugates disclosed herein include, but are not limited to, 20-pi-1,25 dihydroxyvitamin D3; 5-ethynyluracil; abiraterone; aclarubicin; acylfulvene; adecypenol; adozelesin; aldesleukin; all-tyrosine kinase antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; argininedeaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; basic fibroblast growth factor (bFGF) inhibitor, bicalutamide; bisantrene; bisaziridinylspermine; bisnafide; bistratene A; bizelesin; breflate; bleomycin A2; bleomycin B2; bropirimine; budotitane; buthionine sulfoximine; calcipotriol; calphostin C; camptothecin derivatives (e. g., 10-hydroxycamptothecin); canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; and cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; 2'deoxycoformycin (DCF); deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; discodermolide; docosanol; dolasetron; doxifluridine; droloxifene; dronabinol; duocarmycin SA; ebselen; ecomustine; edelfosine; edrecolomab; eflornithine; elemene; emitefur; epirubicin; epothilones; epithilones; epristeride; estramustine analogue; estrogen agonists; estrogen antagonists; etanidazole; etoposide; etoposide 4'-phosphate (etopofos); exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; homoharringtonine (HHT); hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maytansine; mannostatin A; marimastat; masoprocol; maspin; matrilysin inhibitors; matrix metalloproteinase inhibitors; menogaril; merbarone; meterelin; methioninase; metoclopramide; MIF inhibitor; ifepristone; miltefosine; mirimostim; mismatched double stranded RNA; mithracin; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues and derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; podophyllotoxin; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; rapamycin; ras farnesyl protein transferase inhibitors; ras inhibitors; ras-GAP inhibitor, retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. The drug may be an antiproliferative agent, for example piritrexim isethionate, or an antiprostatic hypertrophy agent such as, for example, sitogluside, a benign prostatic hyperplasia therapy agent such as, for example, tamsulosin hydrochloride, or a prostate growth inhibitor such as, for example, pentomone.

In non-limiting embodiments, the drug may be a β-lactam antibiotic. The term "β-lactam antibiotic" refers to the class of antibiotic agents that have a β-lactam ring or derivatized β-lactam ring in their molecular structures. Examples of such β-lactam antibiotics include but are not limited to, penams, including but not limited to, penicillin, benzathine penicillin, penicillin G, penicillin V, procaine penicillin, ampicillin, amoxicillin, methicillin, cloxacillin, dicloxacillin, flucloxacillin, nafcillin, oxacillin, temocillin, mecillinam, carbenicillin, ticarcillin, azlocillin, mezlocillin, and piperacillin; cephems, including but not limited to, cephalosporin C, cefoxitin, cephalosporin, cephamycin, cephem, cefazolin, cephalexin, cephalothin, cefaclor, cefamandole, cefuroxime, cefotetan, cefoxitin, cefixime, cefotaxime, cefpodoxime, ceftazidime, ceftriaxone, cefepime, cefpirome, and ceftaroline; carbapenems and penems including but not limited to, biapenem, doripenem, ertapenem, earopenem, imipenem, primaxin, meropenem, panipenem, razupenem, tebipenem, and thienamycin; and monobactams including but not limited to, aztreonam, tigemonam, nocardicin A, and tabtoxinine β-lactam.

Anti-infective drugs which may be used include but are not limited to quinolones (such as but not limited to nalidixic acid, cinoxacin, ciprofloxacin, norfloxacin, and the like), sulfonamides (e.g., sulfanilamide, sulfadiazine, sulfamethaoxazole, sulfisoxazole, sulfacetamide, and the like), aminoglycosides (e.g., streptomycin, gentamicin, tobramycin, amikacin, netilmicin, kanamycin, and the like), tetracyclines (such as chlortetracycline, oxytetracycline, methacycline, doxycycline, minocycline, and the like), para-aminobenzoic acid, diaminopyrimidines (such as but not limited to trimethoprim, often used in conjunction with sulfamethoxazole, pyrazinamide, and the like), penicillins (such as but not limited to penicillin G, penicillin V, ampicillin, amoxicillin, bacampicillin, carbenicillin, carbenicillin indanyl, ticarcillin, azlocillin, mezlocillin, piperacillin, and the like), penicillinase resistant penicillin (such as but not limited to methicillin, oxacillin, cloxacillin, dicloxacillin, nafcillin, and the like), first generation cephalosporins (such as but not limited to cefadroxil, cephalexin, cephradine, cephalothin, cephapirin, cefazolin, and the like), second generation cephalosporins (such as but not limited to cefaclor, cefamandole, cefonicid, cefoxitin, cefotetan, cefuroxime, cefuroxime axetil, cefinetazole, cefprozil, loracarbef, ceforanide, and the like), third generation cephalosporins (such as but not limited to cefepime, cefoperazone, cefotaxime, ceftizoxime, ceftriaxone, ceftazidime, cefixime, cefpodoxime, ceftibuten, and the like), other beta-lactams (such as but not limited to imipenem, meropenem, aztreonam, clavulanic acid, sulbactam, tazobactam, and the like), beta-lactamase inhibitors (such as but not limited to clavulanic acid), chloramphenicol, macrolides (such as but not limited to erythromycin, azithromycin, clarithromycin, and the like), lincomycin, clindamycin, spectinomycin, polymyxin B, polymixins (such as but not limited to polymyxin A, B, C, D, $E_1$ (colistin A), $E_2$ (colistin B), and the like) vancomycin, bacitracin, isoniazid, rifampin, ethambutol, ethionamide, aminosalicylic acid, cycloserine, capreomycin, sulfones (such as but not limited to dapsone, sulfoxone sodium, and the like), clofazimine, thalidomide, or any other antibacterial agent that can be lipid encapsulated. Anti-infectives can include antifungal agents, including (but not limited to) polyene antifungals (such as but not limited to amphotericin B, nystatin, natamycin, and the like), flucytosine, imidazoles (such as but not limited to miconazole, clotrimazole, econazole, ketoconazole, and the like), triazoles (such as but not limited to itraconazole, fluconazole, and the like), griseofulvin, terconazole, butoconazole ciclopirax, ciclopirox olamine, haloprogin, tolnaftate, naftifine, terbinafine, or any other antifungal that can be lipid encapsulated or complexed and pharmaceutically acceptable salts thereof and combinations thereof.

According to some non-limiting embodiments, the antibiotic drug may include: ampicillin, bacampicillin, carbenicillin indanyl, mezlocillin, piperacillin, ticarcillin, amoxicillin-clavulanic acid, ampicillin-sulbactam, benzylpenicillin, cloxacillin, dicloxacillin, methicillin, oxacillin, penicillin g, penicillin v, piperacillin tazobactam, ticarcillin clavulanic acid, nafcillin, cephalosporin i generation antibiotics, cefadroxil, cefazolin, cephalexin, cephalothin, cephapirin, cephradine cefaclor, cefamandol, cefonicid, cefotetan, cefoxitin, cefprozil, ceftmetazole, cefuroxime, loracarbef, cefdinir, ceftibuten, cefoperazone, cefixime, cefotaxime, cefpodoxime proxetil, ceftazidime, ceftizoxime, ceftriaxone, azithromycin, clarithromycin, clindamycin, dirithromycin, erythromycin, lincomycin, troleandomycin, cinoxacin, ciprofloxacin, enoxacin, gatifloxacin, grepafloxacin, levofloxacin, lomefloxacin, mozzxifloxacin, nalidixic acid, norfloxacin, ofloxacin, sparfloxacin, trovafloxacin, oxolinic acid, gemifloxacin, perfloxacin, imipenem-cilastatin, meropenem, aztreonam, amikacin, gentamicin, kanamycin, neomycin, netilmicin, streptomycin, tobramycin, paromomycin, teicoplanin, vancomycin, demeclocycline, doxycycline, methacycline, minocycline, oxytetracycline, tetracycline, chlortetracycline, mafenide, silver sulfadiazine, sulfacetamide, sulfadiazine, sulfamethoxazole, sulfasalazine, sulfisoxazole, trimethoprim-sulfamethoxazole, sulfamethizole, rifabutin, rifampin, rifapentine, linezolid, streptogramins, quinopristin dalfopristin, bacitracin, chloramphenicol, fosfomycin, isoniazid, methenamine, metronidazol, mupirocin, nitrofurantoin, nitrofurazone, novobiocin, polymyxin, spectinomycin, trimethoprim, colistin, cycloserine, capreomycin, ethionamide, pyrazinamide, para-aminosalicyclic acid, erythromycin ethylsuccinate, and combinations thereof.

One of ordinary skill in the art may make any suitable chemical modifications to the above compounds in order to make reactions of that compound more convenient for purposes of preparing the AuNP conjugates.

In addition, the compositions of the present disclosure may include two or more of any of the drugs/compounds described herein above in combination with any of the AuNP conjugates described or otherwise contemplated herein. In particular non-limiting embodiments, at least one of the two or more drugs/compounds is conjugated to the AuNP conjugate.

While the compositions and methods of the present disclosure are described herein in terms of particular embodiments, it will be apparent to those of ordinary skill in the art that variations may be applied to the compositions and/or methods and in the steps or in the sequence of steps of the methods described herein without departing from the spirit and scope of the inventive concepts as disclosed herein.

EXAMPLES

Examples of the present disclosure are provided hereinbelow. However, it is to be understood that the embodiments of the present disclosure are not be limited to the specific examples, experimentation, results, and laboratory procedures disclosed herein below. Rather, the examples are simply provided as two of various embodiments and are meant to be exemplary, not exhaustive of the inventive concepts described and supported herein.

Example 1

In this example, AuNP-ligand conjugates were formed by coupling AuNPs to a tumor-receptor binding ligand. In at least one embodiment, the ligand was an annexin. In a non-limiting embodiment, the annexin was annexin V (i.e., annexin A5 or ANXA5), forming AuNP-ANXA5. Annexin V is a protein that specifically binds phosphatidylserine (PS) exposed only on the external surfaces of tumor cells and the tumor vasculature. PS is internalized in healthy tissue, thus making ANXA5 a specific target for multiple cancers including breast cancer. ANXA5 is naturally found in humans and mice, making it nontoxic and safe for use. The AuNPs have also been tested clinically to be nontoxic and are also coated in PEG, which shields the particle from the immune system and further prevents toxicity.

The present results show that the contrast of mouse breast tumors grown both in vitro and in vivo using CT imaging is increased 2-3 fold when AuNP-ANXA5 is used, compared to the contrast provided by AuNP not having ANXA5 linked thereto. The AuNP-ANXA5 has a blood clearance of 8 h, and tumor detection as early as 4 h post-injection was observed, thus allowing for quick analysis. Tumors as small as (for example, but not by way of limitation) 4 mm can be detected with CT using AuNP-ANXA5.

Methods

Materials: The plasmid encoding ANXA5, pET-30 Ek/LIC/ANXA5, was previously constructed in this lab (Neves et al., *Nanotechnology* (2013) 24:375104.). Bovine serum albumin (BSA), Alamar Blue reagent, Triton X-100, EDTA, sulfosuccinimidyl 4-(N-maleimidomethyl) cyclohexane-1-carboxylate (sulfo-SMCC), and Tris-acetate-EDTA buffer were from Sigma-Aldrich (St Louis, MO). Sodium phosphate is from Mallinckrodt Chemicals (Phillipsburg, NJ). Paraformaldehyde was from Electron Microscopy Sciences (Hatfield, PA). Antifade reagent Fluoro-gel, borate buffer, FITC (fluorescein isothiocyanate), Matrigel, and Slide-A-Lyzer dialysis cassettes (3.5 kDa) were from Thermo Fisher Scientific (Waltham, MA). The 2 and 100 kDa dialysis membranes were from Spectrum Laboratories (Rancho Dominguez, CA). Anti-ANXA5 (FL-319) was from Santa Cruz Biotechnology (Santa Cruz, CA). Murine breast cancer cells (4T1) and RPMI-1640 were from ATCC (Manassas, VA). Fetal bovine serum (FBS) was from Atlanta Biologicals (Lawrenceville, GA). Antibiotics, penicillin and streptomycin, were from Invitrogen (Grand Island, NY). Gold nanoparticles (avg. size 15 nm) were from Nanoprobes (Yaphank, NY). HS-PEG-NH$_2$ (PEG molecular weight of 3.4 kDa) linker was from Creative PEGWorks (Winston Salem, NC).

ANXA5 production: Recombinant, purified ANXA5 was produced as described by Neves et al. (Neves et al., 2013, op. cit.). ANXA5 was characterized via SDS-PAGE.

AuNP ANXA5 Synthesis: AuNP-ANXA5 was produced using modified protocols as described (Hainfeld et al., *The British Journal of Radiology* (2011) 84:526-33; Takae et al., *Biomacromolecules* (2005) 6:818-24; Ba et al. *Nano Lett* (2010) 10:3006-12). Briefly, AuNPs (15 nm) were initially conjugated to HS-PEG-NH$_2$ (also referred to herein as NH$_2$-PEG-SH) at a molar ratio of 1:4 overnight at 4° C. with stirring. AuNPs were washed three times with PBS and centrifuged at 16,000 g for 20 min. Sulfo-SMCC was added in a 1:2 (w/w) ratio to the AuNP-PEG and incubated for 30 min at room temperature with stirring. AuNP-PEG-sulfo-SMCC was washed three times with PBS and centrifuged at 16,000 g for 15 min. ANXA5 was added in a 1:10 (w/w) ratio and incubated overnight at 4° C. followed by three washes; linkage was possible due to ANXA5 having one SH group that is five amino acids from the carboxy-terminus (FIG. 1 shows a schematic of a process used to produce AuNP-ANXA5 conjugates). Concentration of AuNP was quantified via absorbance at 520 nm, and concentration of ANXA5 was quantified via a Bradford assay.

Dynamic light scattering and zeta-potential: Dynamic light scattering (DLS) and zeta potential for AuNP, AuNP-PEG, and AuNP-ANXA5 nanoparticles were conducted using a Brookhaven ZetaPALS system (Brookhaven Instruments Corporation, Holtsville, NY). Samples were diluted in nanopure water for DLS and 1 M KCl solution for zeta potential.

Transmission electron microscopy: A drop containing either AuNPs or AuNP-ANXA5s was placed on a lacey carbon grid and allowed to dry. Both grids were stained with 1% uranyl acetate for 5 min and washed with nanopure water. Nanoparticles were imaged with a Zeiss 10A transmission electron microscope.

Cell lines and culture conditions: The 4T1 cells were transfected with tdTomato (Td). 4T1-Td cells were grown in RPMI-1640 medium enriched with 10% FBS and penicillin/streptomycin antibiotics (100 U/ml and 100 µg/ml, respectively). The cells were grown at 37° C. with 5% CO$_2$.

In vitro binding strength: The dissociation constant for AuNP-ANXA5 was determined as previously described by Neves et al. (Neves, et al., 2013, op. cit.) using biotin-conjugated AuNP-ANXA5 on 70% confluent 4T1-Td cells. Specific binding was determined by subtracting total binding (medium supplemented with calcium) from nonspecific binding (medium supplemented with EDTA).

In vitro fluorescence visualization: The 4T1-Td cells were grown to 70% confluence on cover slips. AuNP-ANXA5s were tagged with FITC following manufacturer's protocol. FITC-AuNP-ANXA5 (1.5 mg/ml) in 2 mM CaCl$_2$) were incubated with 4T1-Td cells for 2 h followed with PBS washing. The cells were fixed in 4% paraformaldehyde. Images were taken on a Nikon fluorescence microscope.

In vitro microCT contrast enhancement: The 4T1-Td cells were grown to 70% confluence on a T-75 plate. Cells were lifted and incubated with either 1.5 mg/ml AuNP or AuNP-ANXA5s in microcentrifuge vials at 37° C. for 2 h. Cells were washed three times with media and centrifuged at 1000 g for 5 min followed by fixation with 4% paraformaldehyde. Images were taken on a PerkinElmer Quantum GX microCT (Waltham, MA) at 50 keV.

Animal handling procedures: All procedures complied with a protocol approved by the Institutional Animal Care and Use Committee (IACUC) of the University of Oklahoma Health Sciences Center (Oklahoma City, OK). Balb/cJ (Jackson Labs) female mice 6 weeks of age, weighing 18-20 g, were used. Mice were on a standard chow diet.

In vivo tumor model: Mice were injected in mammary fat pad number four with 1×10$^5$ 4 T1-Td mouse breast cancer cells suspended in 50 µl PBS and 50 µl of Matrigel. Mouse body weight and tumor volume were monitored every 3 to 4 days. Tumor volume was calculated with the modified ellipsoid formula volume=(length×width$^2$)/2 using caliper measurements of the longest dimension and perpendicular width. Mice bearing orthotopic 4T1-Td were randomized into groups (6 to 7 per group) prior to the start of the study when tumors reached 100 mm$^3$.

In vivo blood clearance: Blood was collected via submandibular collection over 24 h. Blood clearance was determined based on a modified protocol (Krais et al., Mol. Cancer Ther. (2017) 16:1855-65). Briefly, AuNP-ANXA5s were tagged with biotin following the SeraCare company protocol (SeraCare Life Sciences Inc., Milford, MA). Blood was collected from mice (n=3) between 0-24 h and analyzed via an ELISA sandwich assay using streptavidin-coated high-affinity plates. Plasma dilutions were incubated on streptavidin-coated plates for 2 h at 37° C. Plates were washed and blocked with 1% fetal bovine serum PBS buffer three times. Following washes, wells were incubated for 1 h with 1:5000 dilution of horseradish peroxidase (HRP) conjugated goat anti-mouse IgG and IgM. The wells were developed with o-phenylenediamine (OPD) for quantification on a BioTek Synergy plate reader (BioTek, Winooski, VT). A standard curve of varying concentrations of biotinylated AuNP-ANXA5 was generated.

In vivo targeted accumulation of targeted AuNPs: Mice (n=6-7) were injected with 250 mg/kg AuNP or AuNP-ANXA5 intravenously when tumors reached 100 mm$^3$. Mice were imaged with a Flex X-O X-PET animal imager (Gamma Medica Ideas, Northridge, CA) at 50 keV with 256 slices before the injection and for 12 h after. Gold concentration was determined by quantifying CT intensity at the tumor against the control image using the Amira software. Intensity was correlated to a gold standard curve previously generated. Percent injected dose was calculated using the following equation:

$$\text{Injected Dose}(\%) = \frac{\text{Concn. of AuNP at tumor(mg/ml)} \times \text{Volume of tumor(ml)}}{\text{Amount of injected AuNP(mg)}} \times 100$$

The concentration of AuNP or AuNP-ANXA5 at the tumor was calculated with a pre-determined standard curve comparing change in contrast to concentration of gold nanoparticles.

Statistics: Statistical significance of in vitro and in vivo contrast enhancement studies was assessed using a one-way ANOVA and Tukey-Kramer multiple comparisons test at p<0.05 with GraphPad Prism software.

Results

Characterization of AuNP-ANXA5s

Multiple analyses (UV-vis spectroscopy, agarose gel, DLS, and zeta potential) were conducted on the particles, confirming the addition of ANXA5 as well as the maintenance of the key characteristics of AuNPs that make it a contrast agent. Analysis via UV-vis spectroscopy showed that the particles retained their characteristic properties, as seen in the similar absorbance spectrums in FIG. 2A of AuNP against AuNP-ANXA5.

Table 1 further depicts the transition in size and surface modification of the particle, as seen in the increasing hydrodynamic diameters (AuNP<AuNP-PEG<AuNP-ANXA5) of the particles. The surface charge of the nanoparticle also changes with the addition of PEG and ANXA5, as seen in the zeta potential in Table 1. Since ANXA5 is a negatively charged protein, the surface of the nanoparticle becomes more negative with the addition of ANXA5 as compared to the particle only coated in PEG.

TABLE 1

Dynamic Light Scattering (DLS) and Zeta Potential for Nanoparticles

| Sample | Hydrodynamic Diameter (nm) | Zeta Potential (mV) |
| --- | --- | --- |
| AuNP | 58.8 ± 0.6 | −5.6 |
| AuNP · PEG | 80.6 ± 1.8 | −0.6 |
| AuNP-ANXA5 | 101.6 ± 1.0 | −5.44 |

Data represented as mean ± SEM (n = 3).

Figure 2:
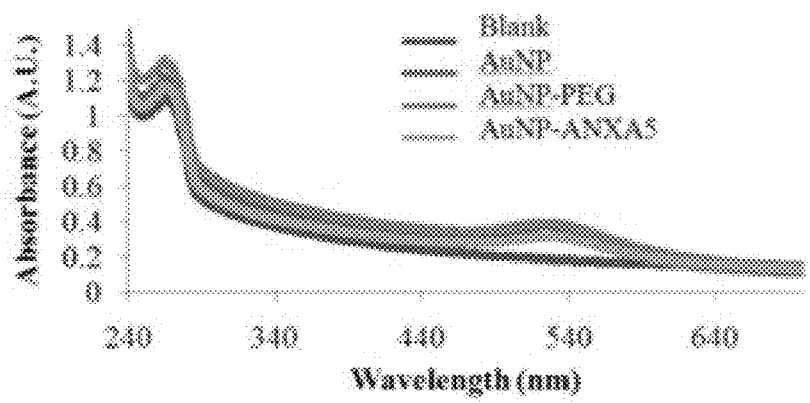
FIG. 2 shows a characterization of AuNP-ANXA5 particles. (A) Absorbance spectrum of gold nanoparticles, showing no change with the addition of PEG or ANXA5. (B) A transmission electron microscopy image of single gold nanoparticles (black circle) coated with ANXA5 protein (hazy, gray region). Scale bar is 15 nm. (C) Fluorescent microscopy showing localization of tdTomato-labeled 4T1 cancer cells (left) and FITC-labeled AuNP-ANXA5 (right). Scale bar is 25 μm.
Figure 2:
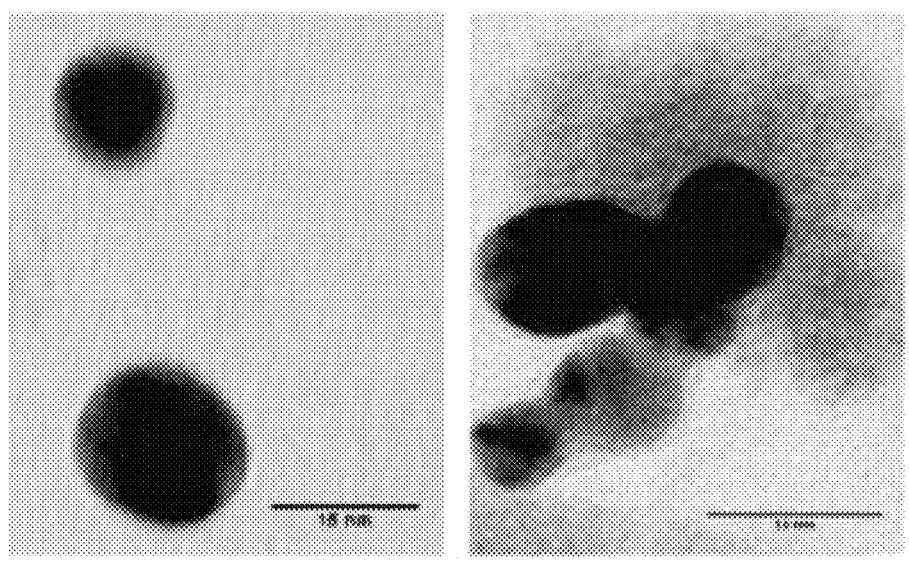
Figure 2:
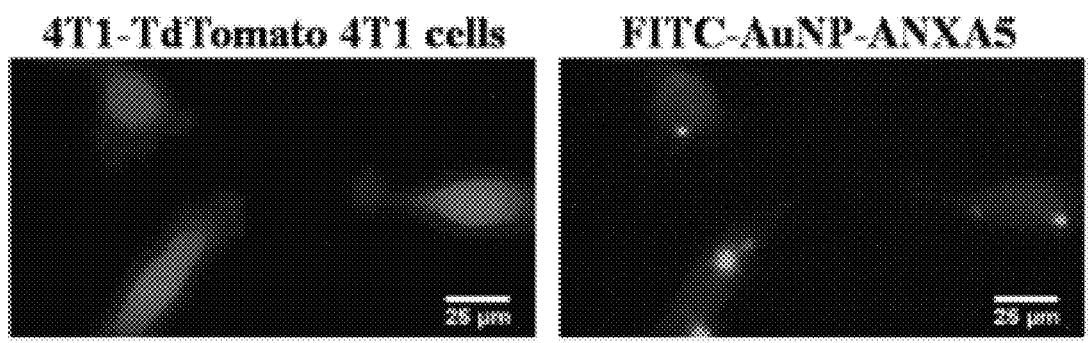

To visualize the nanoparticles coated in ANXA5 protein, transmission electron microscopy (TEM) with staining for protein presence was conducted on AuNP and AuNP-ANXA5. FIG. 2B shows individual gold nanoparticles (dark black circles) with the ANXA5 protein (hazy, dark gray region) directly attached to the surface.

In Vitro Confirmation

The dissociation constant for binding of the AuNP-ANXA5s specifically to 4T1 breast cancer cells was determined to be 60±68 pM. This strong affinity can be visualized in FIG. 2C with the localization of FITC-labeled AuNP-ANXA5s with tdTomato red fluorescently labeled 4T1 breast cancer cells.

A preliminary imaging study with 4T1 breast cancer cells and either AuNP or AuNP-ANXA5 followed by CT via a PerkinElmer Quantum GX microCT (Waltham, MA) was conducted. Breast cancer cells that were incubated with only AuNP had only an approximately 2-fold increase in contrast compared to cells with no nanoparticles. Cells incubated with AuNP-ANXA5 had an approximately 4.5-fold increase in contrast.

In Vivo Confirmation

Figure 3:
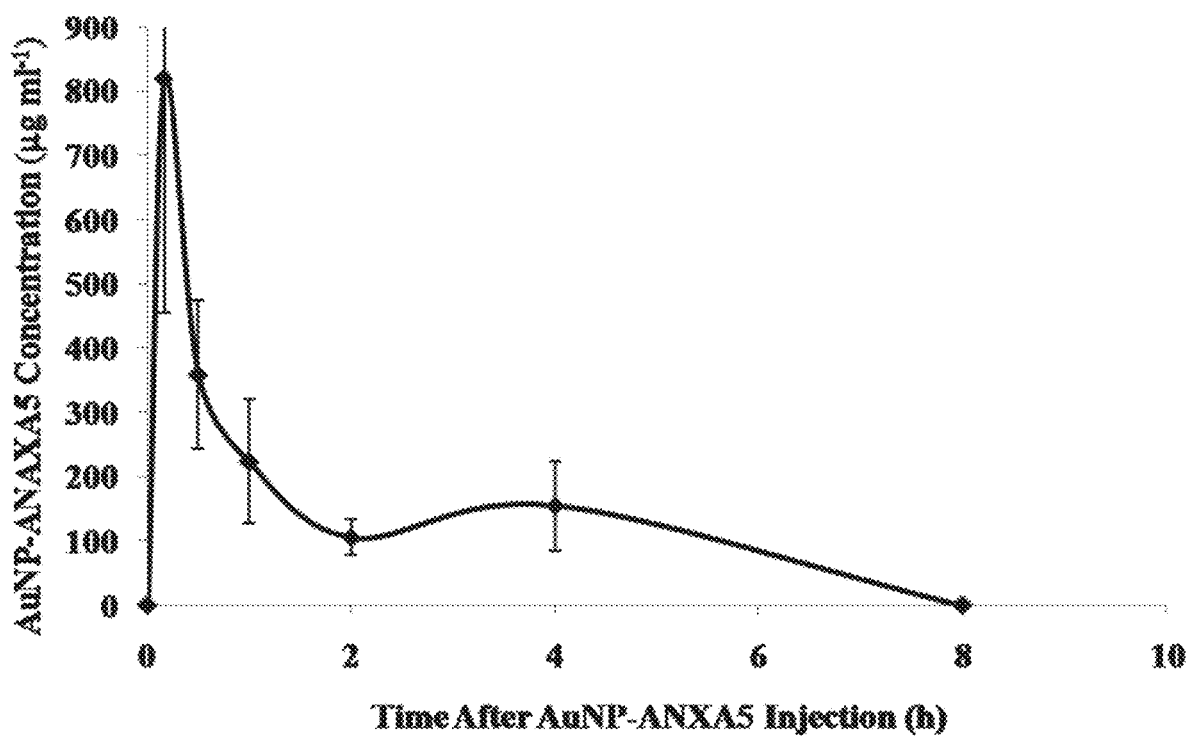
FIG. 3 shows clearance from the blood of AuNP-ANXA5 particles. Balb/c mice with orthotopic 4T1 breast tumors (n=3) were injected with biotinylated AuNP-ANXA5s, and blood was collected between 10 min to 24 h post-injection. After 8 h, no AuNP-ANXA5s were detectable in the blood of the mice.

An animal study on mice with orthotopic 4T1 breast tumors in the mammary fat pad was conducted to determine how long the AuNP-ANXA5s remained in the blood. As seen in FIG. 3, the gold nanoparticles were cleared from the bloodstream within eight hours.

Figure 4:
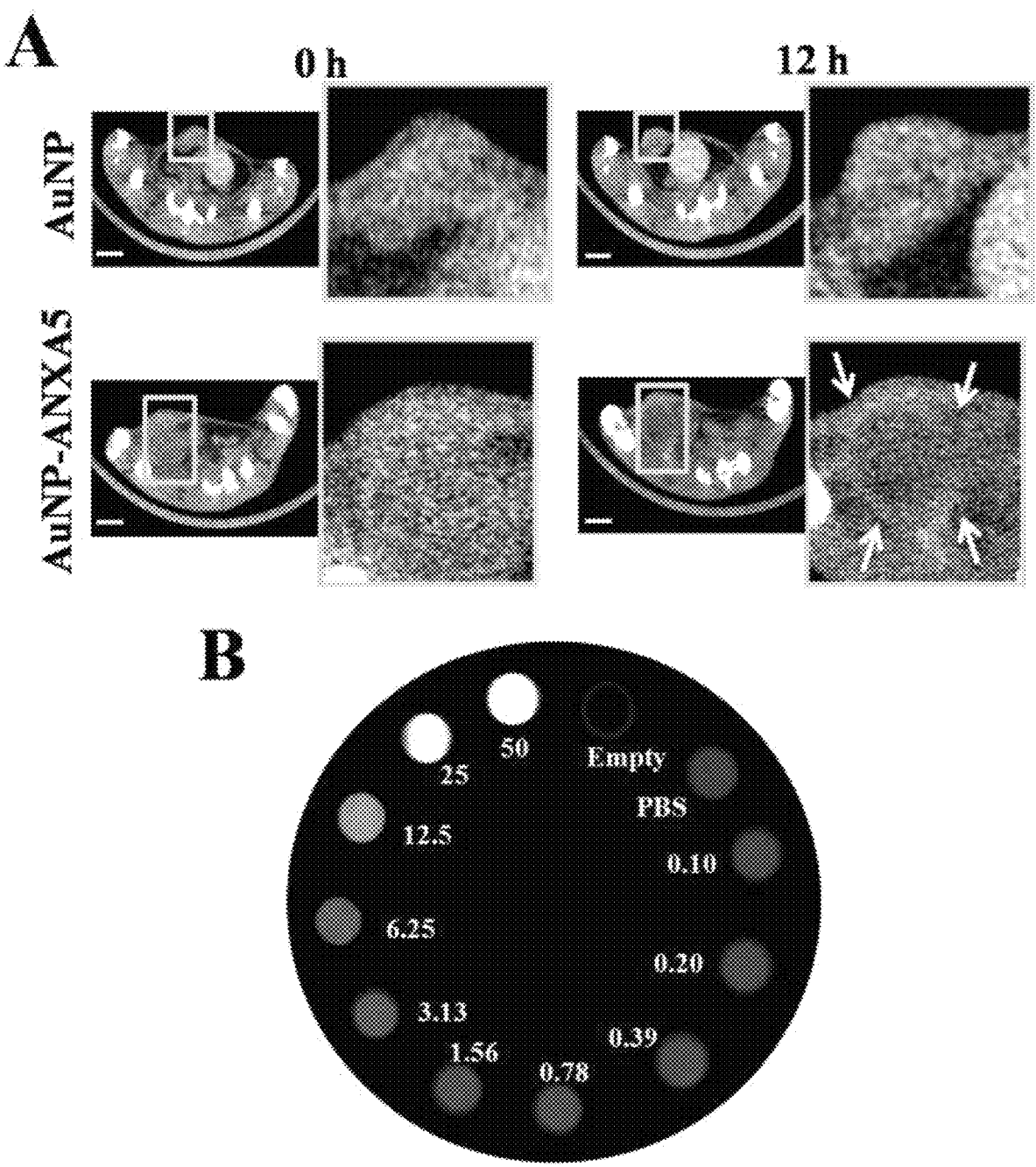
FIG. 4 shows representative CT images of mice injected with AuNP-ANXA5s. Mice were imaged before and 12 h after injection of either 250 mg/kg of AuNPs or AuNP-ANXA5s. (A) In the mouse injected with AuNPs, it is difficult to identify the tumor compared to the remainder of the animal. In the mouse injected with AuNP-ANXA5s, a clear border of the tumor is significantly brighter (white arrows) where the gold nanoparticles have accumulated. Scale bar is 4 mm. (B) Representative CT images of intensity versus concentration of AuNP-ANXA5 (mg/ml).

A second animal study comparing targeted versus untargeted gold nanoparticles was conducted to evaluate the clinical relevance of using AuNP-ANXA5s for detection of breast cancer. Mice were injected intravenously (i.v.) with 250 mg/kg (5 mg) of either AuNPs or AuNP-ANXA5s, and CT scans were conducted over time to compare tumor accumulation of nanoparticles. FIG. 4A shows representative CT images of mice with small 4T1 breast tumors 12 h after delivery of either AuNP or AuNP-ANXA5. When comparing the tumors before injection of nanoparticles versus after, the mice injected with AuNP-ANXA5s have a strong, bright border around the rim of the tumor where the gold nanoparticles have accumulated in the tumor as well as on the tumor vasculature. On the other hand, the untargeted AuNP-injected mice have minimal increase in contrast. FIG. 4B shows comparisons of density of CT image intensity versus concentration of AuNP-ANXA5 (mg/ml).

Figure 5:
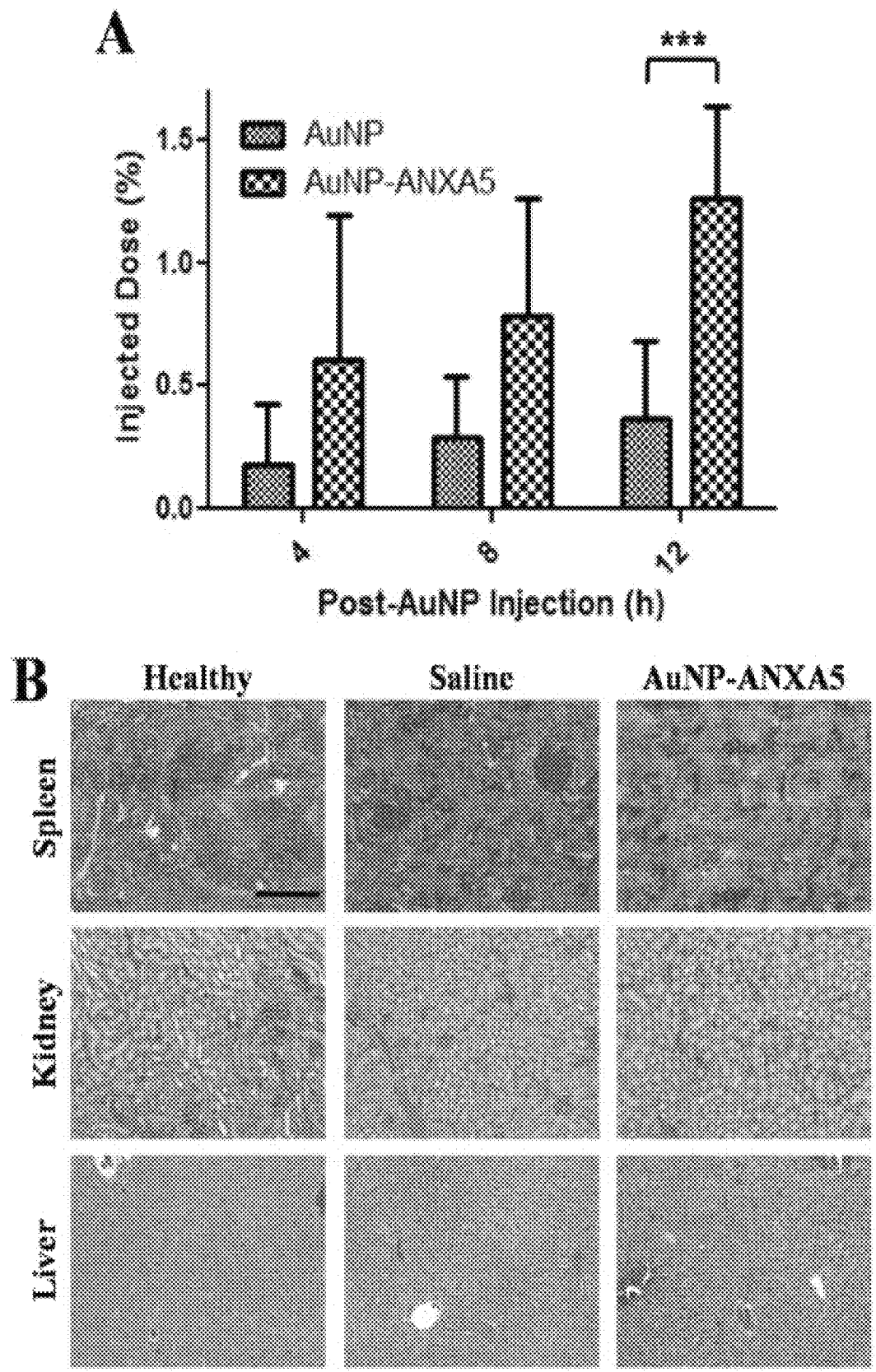
FIG. 5 shows in vivo accumulation of targeted versus untargeted AuNPs. (A) Mice with orthotopic breast cancer (4T1) tumors were injected with either AuNPs or AuNP-ANXA5s and imaged over a 12 h period to evaluate accumulation at the site of the tumor. A dose of 250 mg/kg was given per animal, which is significantly lower than the LD$_{50}$ (5000 mg/kg). Mice injected with AuNP-ANXA5s had significant accumulation of nanoparticles compared to AuNP-injected mice as early as 4 h after injection. Data represented as mean±SEM (n=5-7). Statistical significance indicated as *** ($p<0.001$). (B) H&E representative images of spleen, liver, and kidney, indicating no morphological damage due to AuNP-ANXA5. No signs of mouse stress or toxicity were detected during the course of the study. Scale bar is 100 μm.

The images in FIG. 4A were taken for multiple mice (n=5-7) injected with either AuNP or AuNP-ANXA5 and analyzed for accumulation of gold nanoparticles at the tumor as percent injected dose. As seen in FIG. 5A, tumors of mice with AuNP-ANXA5 had significantly higher accumulation of nanoparticles compared to untargeted nanoparticles starting as early as 4 h and continuing for 12 h. There is a 3-fold increase in concentration of gold nanoparticles when comparing targeted versus untargeted nanoparticles. FIG. 5B demonstrates H&E stained representative images confirming no damage to the clearance organs due to AuNP-ANXA5.

Discussion

Breast cancer has a 94% survival rate if diagnosed early. However, when diagnosed during late stage, the survival rate for breast cancer falls to only 10%. Mammograms are the current gold standard for breast cancer diagnosis, but they have up to a 12% false positive rate, usually due to the failure of differentiating tumors from dense breasts. False positive rates also increase in women who have undergone biopsies for previously misidentified tumor presence. In order to decrease these rates as well as prevent unnecessary procedures, a novel targeted gold nanoparticle has been developed with computed tomography as an alternative to diagnose breast cancer earlier and with more specificity. Gold nanoparticles are surface modified with annexin V, which binds specifically to phosphatidylserine exposed on tumor cells and tumor vasculature. CT, a widely available imaging modality, can be used to detect the presence of breast cancer with higher sensitivity and specificity than the current standard of care.

Targeted gold nanoparticles were developed and characterized using DLS, zeta-potential, UV-vis spectroscopy, and TEM. Changes in the hydrodynamic diameter and zeta potential confirmed addition of PEG and ANXA5 to the surface of gold nanoparticles. PEG acts a protective polymer, shielding the gold nanoparticles from the immune system by minimizing recognition, as seen in the more neutral zeta-potential of the gold nanoparticles. ANXA5 is a negatively charged protein, which causes a negative shift in zeta-potential of the PEG coated gold nanoparticles as well as an increase in the overall hydrodynamic diameter.

Nanoparticles accumulate within the tumor via two pathways, passively via the enhanced permeation and retention (EPR) effect and actively via targeting ligands. The EPR effect is caused by a combination of the leaky, immature blood vessels that allow for permeation of the nanoparticles and the imperfect lymphatic drainage system, which prevents clearance of the nanoparticles. The leaky vasculature is most effective in accumulating nanoparticles between 10-100 nm; the AuNP-ANXA5 nanoparticles are at the upper end of this range (102 nm) and thus should be optimal for EPR accumulation.

The addition of active targeting of AuNP-ANXA5 to the vasculature as well as to tumor cells increases the overall accumulation of gold nanoparticles for increased contrast. In vitro studies showed specific binding of AuNP-ANXA5 to 4T1 breast cancer cells via fluorescent microscopy. Strong colocalization of Tdtomato transfected 4T1 cells and FITC-tagged AuNP-ANXA5 confirmed ANXA5 directed binding. Previous literature has shown that ANXA5 causes endocytosis, which would explain the vesicle like fluorescent aggregates colocalized within the 4T1 cells. The strength of the colocalization is further confirmed in the low dissociation constant for binding to 4T1 cells, indicating strong binding. Previous studies have also confirmed strong binding of ANXA5 to tumor vasculature representing non-confluent endothelial cells.

In vivo studies confirmed plasma clearance of AuNP-ANXA5s within 8 h post-injection and tumor identification as soon as 4 h after injection. AuNP-ANXA5s had a 2-3-fold increase in contrast compared to control AuNPs 12 h post-injections. Tumors as small as 4 mm were identifiable, making AuNP-ANXA5 a promising modality for early diagnosis of breast cancer compared to the 10-20 mm detection limit of mammograms (Welch et al., *New England Journal of Medicine* (2016) 375:1438-47). Tumors even smaller than 4 mm can be detected by this imaging that is based on targeting the tumor vasculature, since tumors need their own blood vessels for supplying oxygen and nutrients to grow beyond 1-2 mm. The AuNPs have an $LD_{50}$ of 100 mg (5000 mg/kg) per animal as evaluated by the company (Nanoprobes Inc.). Doses as high as 1100 mg/kg have been tested in mice with no detectable toxicity. Our dose of 5 mg per animal (250 mg/kg) is significantly lower than the cytotoxic dose.

Recent studies using targeted gold nanoparticles showed similar increases in contrast in vitro and in vivo against larynx and oral cancer, glioblastoma, and lymph nodes as compared to untargeted nanoparticles (Hainfeld et al., *The British Journal of Radiology* (2011) 84:526-33; Popovtzer et al., *Nano Lett.* (2008) 8:4593-6; Lai et al., *Journal of Nanobiotechnology* (2015) 13:85; Reuveni et al., *International Journal of Nanomedicine* (2011) 6:2859; and Eck et al., *Nano Lett.* (2010) 10:2318-22).

An earlier study using Her2 targeted gold nanoparticles showed an increase in contrast compared to untargeted nanoparticles at doses of 1100 mg/kg to 310 mg/kg, which is significantly higher than the proposed dose of 250 mg/kg as well as limiting detection to only breast tumors expressing Her2. Compared to other targeted nanoparticles, a key advantage of the technology described herein is the broad applicability for detection of multiple cancers, such as bladder, ovarian, melanoma, and lung, due to the expression of PS on the surface of the tumors as well as the tumor vasculature. These tumors currently do not have effective diagnostic modalities that are sensitive as well as widely available to the general public.

Current diagnostics require expensive and scarcely available tools such as MRI systems with the risk of still getting false positives and negatives. Due to a lack of a cost-effective and widely available imaging modality with three-dimensional capabilities to minimize dense breast issues, most patients are diagnosed during late stages of tumor development, at which point the effectiveness of surgery and chemotherapy has significantly decreased. The technology described herein could be an effective alternative for the universal detection of multiple cancers using CT, which is already widely present in all clinics and hospitals. The use of AuNP-ANXA5 (or other AuNP conjugates described herein), a novel, targeted contrast agent for early detection of breast cancer, in conjunction with computed tomography, can provide an alternative cost-effective diagnostic tool with more precision and accuracy for multiple malignancies, including (but not limited to) breast cancer.

In conclusion, AuNP-ANXA5 conjugates have been developed, and their efficacy has been evaluated in cell culture as well as in an orthotopic mouse model, showing significant increases in detection of breast tumors with targeted versus untargeted gold nanoparticles. Gold nanoparticles have minimum toxicity and are currently being tested in phase I clinical trials for therapy based applications (Libutti et al., *Clinical Cancer Research* (2010) 0978; and Anselmo et al., *Bioengineering & Translational Medicine* (2016) 1:10-29). Combined with ANXA5, which is a naturally occurring human protein, the targeted nanoparticle contrast agent has the capability of being a universal diagnostic tool for early cancer detection of multiple malignancies (including but not limited to breast, ovarian, melanoma, and bladder cancer).

Example 2

Synthesis of AuNP-Annexin V-Chlorambucil

This example shows a non-limiting embodiment of the synthesis of an AuNP-Annexin V-drug conjugate in accordance with the present disclosure. In this example, chlorambucil (CHL) is conjugated to Annexin-V to form annexin V-CHL, which is then conjugated to AuNPs surface-functionalized with HS-PEG-NH$_2$ linker groups.

I. Functionalization of AuNPs:

AuroVist™-15 nm (4° C.) initially at 200 mg ml$^{-1}$ Phosphate buffered saline (PBS): AuNPs are diluted to (20 mg/ml, 0.1 M) in PBS to a final volume of 0.5 ml. 50 µl of 200 mg/ml solution is present in 0.45 ml of PBS.

PEGylating AuNPs: 61.2 mg (0.36 M) HS-PEG-NH$_2$ linker (3.4 kDa, −20° C.) is diluted in 0.5 ml of PBS (6:1 weight ratio spacer:AuNPs). The spacer solution is sonicated for 15 min in a water bath sonicator. HS-PEG-NH$_2$ solution is added dropwise to the AuNPs solution and placed on a rotator. The solution is allowed to stir overnight on the rotator at 4° C.

Purifying AuNP-S-PEG-NH$_2$ solution: Excess linker is washed away 3 times, and the solution is pipetted into an ultracentrifuge tube. The tube is washed with PBS, and the wash buffer is placed with nanoparticles. The remaining ultracentrifuge tube space is filled with PBS. The tube is then centrifuged at 16,000×g for 20 min.

II. Conjugation of Chlorambucil (CHL) to Annexin V:

1000 µg of chlorambucil (4° C.) is dissolved in 50 µL of an acid alcohol solution (3% HCl (12 M) and 95% EtOH v/v). The mixture is diluted in 1 mL of phosphate buffer (20 mM). The buffer at pH 7.4 is added drop by drop and stirred. This provides a larger working volume of chlorambucil to continue downstream production. 100 mg of 1-ethyl-3-[3-dimethylaminopropyl] carbodiimide hydrochloride (EDC) is added; the EDC will bind the carboxylic groups of chlorambucil, increasing their chemical reactivity towards primary amines. 70 mg of sulfo-NHS (4° C.) is added; N-hydroxysulfosuccinimide (Sulfo-NHS) stabilizes the EDC activated carboxylic groups, increasing the efficiency of the chlorambucil-annexin reaction. Then the solution is stirred vigorously for 10 min. Then 2 µL of β-mercaptoethanol is added; β-mercaptoethanol neutralizes the excess EDC and NHS, preventing their interference in downstream reactions. Then the solution is immediately titrated to a pH of 7.4; raising the pH stabilizes the sensitive chlorambucil functional groups. 10 mL of a 1 mg/ml solution of annexin V (−80° C.) in phosphate buffer (20 mM) is then added, and chlorambucil-NHS is added drop by drop to the buffered annexin V. Then the solution is stirred gently for 12 hours at 4° C. followed by centrifuging for 1 h at 4° C. and 10,000×g. Chlorambucil is not stable in neutral pH solutions and will precipitate. The precipitate is easily removed by centrifugation. The supernatant is carefully collected, and the pellet is discarded. The supernatant is dialyzed against 2 L of phosphate buffered (30 mM) saline for 8 h at 4° C. with a 25 kDa MWCO regenerated cellulose filter (Dialysis membrane: Slide-A-Lyzer dialysis cassettes, 3.5 kDa), and the dialysate is switched twice during this time. This step removes the rest of the unbound chlorambucil as well as other upstream contaminants such as β-mercaptoethanol.

III. Conjugation of Annexin V-CHL to AuNP-S-PEG-NH$_2$:

Adding maleimide groups to NH$_2$ functionalized AuNPs: 1 mg Sulfo-SMCC (−20° C.) in 0.5 ml PBS is added. The purified AuNP-S-PEG-NH$_2$ in sulfo-SMCC PBS buffer is redispersed with water bath/probe sonicator for 10-15 min. The reaction is allowed to stir for 30 min on a rotator at room temperature.

Purifying AuNP-SMCC solution: Excess crosslinker is washed away, and the solution is pipetted into an ultracentrifuge tube. The tube is washed with PBS, and the wash buffer is placed with the nanoparticles. The remaining ultracentrifuge tube space is filled with PBS, and the tubes are centrifuged at 16,000×g for 20 min. The supernatant is removed, and the pellet is redispersed in 0.5 ml PBS with water bath/probe sonicator until total dispersion.

Adding annexin V-CHL (−80° C.) to maleimide functionalized AuNPs: annexin V is added to Sulfo-SMCC at a 2:1 weight concentration ratio, and the reaction is allowed to shake 18 h under moderate speed at 4° C. The vial should be stabilized in a Styrofoam box and parallel to ensure proper circulation.

Blocking leftover maleimide groups on AuNP-annexin V-CHL: 1.5 mg L-cysteine is dissolved in 1 mL PBS and vortexed for a minute to dissolve. 10 µl L-cysteine solution is added to AuNP-annexin V-CHL and allowed to shake 1 h under moderate speed at 4° C.

Purifying AuNP-annexin V-CHL solution: excess annexin V-CHL is washed away, and the solution is pipetted into an ultracentrifuge tube. The tube is washed with PBS, and the wash buffer is placed with the nanoparticles. The remaining ultracentrifuge tube space is filled with PBS, and the tube is centrifuged at 12,000×g for 15 min. The supernatant is removed, and the pellet is redispersed in a desired volume of PBS buffer with water bath/probe sonicator.

The solution is then dialyzed in 100 kDa dialysis membrane for 4 h against 2 L of PBS, and the concentration of AuNP, annexin V, and CHL in the final product are measured. The AuNP-annexin V-CHL conjugate is stored at 4° C.

Cell Viability Assay for AuNP-Annexin V-Drug Conjugate

The following cell viability assay can be used to determine the effect (toxicity) of the AuNP-annexin V-drug conjugate on cells in vitro. Harvest 5×10$^6$ cells previously cultured in T-75 flasks and dilute to a total of 25 mL with media. Seed each well of a 96-wells plate with 180 µL of media containing 20,000 cells, and allow cell attachment for at least 24 hours. Then treat groups according to the following experimental protocol.

Groups: (i) Untreated cells; (ii) Cells treated with different concentrations of the drug dissolved in DMSO or other solvent; (iii) Cells treated with different concentrations of annexin V-drug conjugate; and (iv) Cells treated with different concentrations of AuNP-annexin V-drug conjugate.

A range of 1×10$^2$ to 1×10$^{-2}$ µM of drug can be used in a non-limiting embodiment of this assay. For reproducibility, there should be 6 wells for each condition (each concentration in each group).

Incubate cells with chosen treatment for 20 h. Add 20 µL of Alamar Blue solution to each well and incubate cells with Alamar Blue for 4 h to allow dye uptake. Read the absorbance immediately at 540 nm. Determine toxicity of treatment group.

While the present disclosure has been described herein in connection with certain embodiments so that aspects thereof may be more fully understood and appreciated, it is not intended that the present disclosure be limited to these particular embodiments. On the contrary, it is intended that all alternatives, modifications, and equivalents are included within the scope of the present disclosure as defined herein. Thus the examples described above, which include particular embodiments, will serve to illustrate the practice of the inventive concepts of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the present disclosure. Changes may be made in the formulation of the various compositions described herein, the methods described herein or in the steps or the sequence of steps of the methods described herein without departing from the spirit and scope of the present disclosure. Further, while various embodiments of the present disclosure have been described in claims herein below, it is not intended that the present disclosure be limited to these particular claims.

What is claimed is:

1. A method of therapeutic treatment of a cancerous tissue in a subject in need of such therapy, the method comprising the step of:
    administering to the subject a gold nanoparticle (AuNP)-drug conjugate, comprising:
    heterobifunctional PEG linker groups linked to a surface of the AuNP;
    an annexin protein conjugated to the AuNP via the sulfo-succinimidyl 4-(N-maleimidomethyl) cyclohexane-1-carboxylate (sulfo-SMCC) groups which are linked to the heterobifunctional PEG linker groups; and
    a therapeutic drug conjugated to the annexin protein via 1-ethyl-3-[3-dimethylaminopropyl] carbodiimide hydrochloride (EDC) linker groups, and wherein the therapeutic drug is chlorambucil.

2. The method of claim 1, wherein the annexin is annexin V.

3. The method of claim 1, further comprising the steps of:
    allowing the AuNP-drug conjugate to bind to and/or penetrate into the cancerous tissue of the subject; and
    exposing a dosage of X-ray radiation to the cancerous tissue.

* * * * *

UNITED STATES PATENT AND TRADEMARK OFFICE
CERTIFICATE OF CORRECTION

PATENT NO. : 12,178,889 B2
APPLICATION NO. : 17/269113
DATED : December 31, 2024
INVENTOR(S) : Roger G. Harrison, Jr. and Needa A. Virani Page 1 of 1

It is certified that error appears in the above-identified patent and that said Letters Patent is hereby corrected as shown below:

In the Specification

Column 19, Line 5: Delete "fl-lactam" and replace with -- β-lactam --

Signed and Sealed this
Eighteenth Day of February, 2025

Coke Morgan Stewart
*Acting Director of the United States Patent and Trademark Office*